United States Patent
Abbott et al.

(10) Patent No.: US 7,270,653 B2
(45) Date of Patent: *Sep. 18, 2007

(54) METHODS OF TREATING ABNORMAL BIOLOGICAL CONDITIONS USING METAL OXIDES

(75) Inventors: Chun Lim Abbott, Pittsburgh, PA (US); Dominic Abbott, Pittsburgh, PA (US); Meir Sacks, Pittsburgh, PA (US)

(73) Assignee: Abbott Research Group, Pittsburgh, PA (US)

( * ) Notice: Subject to any disclaimer, the term of this patent is extended or adjusted under 35 U.S.C. 154(b) by 24 days.

This patent is subject to a terminal disclaimer.

(21) Appl. No.: 10/847,299

(22) Filed: May 18, 2004

(65) Prior Publication Data

US 2004/0215164 A1 Oct. 28, 2004

Related U.S. Application Data

(63) Continuation-in-part of application No. 10/371,395, filed on Feb. 20, 2003, which is a continuation-in-part of application No. 10/077,256, filed on Feb. 20, 2002, now Pat. No. 6,589,216.

(60) Provisional application No. 60/472,167, filed on May 21, 2003.

(51) Int. Cl.
*A61M 31/00* (2006.01)
(52) U.S. Cl. .................................................... 604/515
(58) Field of Classification Search ........ 604/275–279, 604/330, 385.17, 514, 39, 48, 73, 257, 259, 604/212, 517, 515
See application file for complete search history.

(56) References Cited

U.S. PATENT DOCUMENTS

| | | | |
|---|---|---|---|
| 7,668 | A | 7/1833 | Harrington |
| 7,982 | A | 1/1834 | Harrington |
| 8,736 | A | 3/1835 | Harrington |
| 4,176 | A | 9/1845 | Harrington |
| 60,526 | A | 12/1866 | Landis |
| 77,539 | A | 5/1868 | Scherenell et al. |
| 341,142 | A | 5/1886 | Hamilton et al. |
| 362,778 | A | 5/1887 | Payne |
| 452,222 | A | 5/1891 | Haughawout |

(Continued)

FOREIGN PATENT DOCUMENTS

EP 1 072 268 A1 1/2001

(Continued)

OTHER PUBLICATIONS http://www.sh.Isuhsc.edu/fammed/OutpatientManual/VaginitisSTDs.htm.*

(Continued)

*Primary Examiner*—Matthew DeSanto

(57) ABSTRACT

A method of treating an abnormal biological condition involves the steps of introducing a metal oxide into the vaginal canal and repeating the step of introducing at regular intervals to treat an abnormal biological condition. The abnormal biological condition treated in accordance with the present invention may be symptomatic or asymptomatic. Treating may involve treating at least one of an abnormal fungal, bacterial, biofilm, viral, inflammatory or neoplastic biological condition.

12 Claims, 7 Drawing Sheets

U.S. PATENT DOCUMENTS

| | | |
|---|---|---|
| 471,514 A | 3/1892 | Reutter |
| 494,520 A | 3/1893 | Boyd |
| 505,393 A | 9/1893 | Dawdy et al. |
| 520,206 A | 5/1894 | Hinkley |
| 520,895 A | 6/1894 | Petit |
| 527,788 A | 10/1894 | Hebard |
| 563,387 A | 7/1896 | Keller |
| 578,611 A | 3/1897 | Rively |
| 593,318 A | 11/1897 | Bacon |
| 632,728 A | 9/1899 | Lander |
| 635,004 A | 10/1899 | Souder |
| 662,716 A | 11/1900 | Gaedeke |
| 676,269 A | 6/1901 | Newbury |
| 756,252 A | 4/1904 | Locke |
| 932,775 A | 8/1909 | Gaston |
| 937,292 A | 10/1909 | Eichholtz |
| 1,042,624 A | 10/1912 | Wagoner |
| 1,045,326 A | 11/1912 | Ruflin |
| 1,098,220 A | 5/1914 | Borsody |
| 1,149,971 A | 10/1915 | Wagoner |
| 1,167,979 A | 1/1916 | Clarke |
| 1,195,933 A | 8/1916 | Wagoner |
| 1,338,464 A | 4/1920 | Shafer |
| 1,566,061 A | 12/1925 | Ziegler |
| 1,593,106 A | 7/1926 | Shoub |
| 1,628,843 A | 5/1927 | Horton |
| 1,922,006 A | 8/1933 | von Hoessle |
| 2,347,567 A | 4/1944 | Kresse |
| 3,479,130 A | 11/1969 | Rapaport |
| 3,860,707 A | 1/1975 | Wootton |
| 3,916,896 A | 11/1975 | Ballard |
| 4,382,886 A | 5/1983 | Sosnowski |
| 4,401,651 A | 8/1983 | Knutson |
| 4,701,164 A | 10/1987 | Casson et al. |
| 4,923,677 A | 5/1990 | Simon et al. |
| 4,950,231 A | 8/1990 | Liu |
| 5,158,774 A * | 10/1992 | Inman ........................ 424/430 |
| 5,292,532 A | 3/1994 | Bombart |
| 5,518,733 A | 5/1996 | Lamothe et al. |
| 5,520,664 A | 5/1996 | Bricault, Jr. et al. |
| 5,577,514 A | 11/1996 | Zimmerman |
| 5,622,927 A | 4/1997 | Hangay et al. |
| 5,695,481 A | 12/1997 | Heinzelman et al. |
| 5,766,632 A | 6/1998 | Oldham et al. |
| 5,840,771 A | 11/1998 | Oldham et al. |
| 5,946,741 A | 9/1999 | Moon |
| 6,066,338 A | 5/2000 | Oldham et al. |
| 6,074,671 A | 6/2000 | Oldham et al. |
| 6,153,208 A | 11/2000 | McAtee et al. |
| 6,159,174 A | 12/2000 | Oldham et al. |
| 6,190,365 B1 * | 2/2001 | Abbott et al. ................ 604/279 |
| 6,190,678 B1 | 2/2001 | Hasenochrl et al. |
| 6,238,686 B1 | 5/2001 | Burrell et al. |
| 6,248,343 B1 | 6/2001 | Jampani et al. |
| 6,296,880 B1 | 10/2001 | Murad |
| 6,319,510 B1 | 11/2001 | Yates |
| 6,338,855 B1 | 1/2002 | Albacarys et al. |
| 6,342,208 B1 | 1/2002 | Hyldgaard et al. |
| 6,368,586 B1 * | 4/2002 | Jacob et al. .............. 424/78.08 |
| 6,436,422 B1 | 8/2002 | Trogolo et al. |
| 6,447,490 B1 * | 9/2002 | Liu et al. ..................... 604/279 |
| 6,522,918 B1 * | 2/2003 | Crisp et al. ................... 604/20 |
| 6,589,216 B1 | 7/2003 | Abbott et al. |
| 6,630,172 B2 | 10/2003 | Batarseh |
| 6,723,350 B2 | 4/2004 | Burrell et al. |
| 2001/0046526 A1 | 11/2001 | Greenfelder |
| 2002/0001600 A1 | 1/2002 | Oldham et al. |
| 2002/0001604 A1 | 1/2002 | Shigeru et al. |
| 2003/0118664 A1 | 6/2003 | Trogolo et al. |

FOREIGN PATENT DOCUMENTS

| | | |
|---|---|---|
| GB | 2 112 285 A | 7/1983 |

OTHER PUBLICATIONS

Internet article, "Emerging challenges in bacterial vaginosis", Paul Nyirjesy, MD, Nov. 1, 2000, 12 pages.

Product brochure, The Odor Steeler™ from iSi North America, obtained from the Internet, Mar. 19, 1999, 5 pgs.

Publication. "Vaginal Douching Is Not All That Bad", M.E. Boon et al, 17 pages.

Publication. "Processes of Bioadhesion on Stainless Steel Surfaces and Cleanability: A Review with Special Reference to The Food Industry", Laurence Boulangé-Petermann, *Biofouling*, 1996, vol. 10(4), pp. 275-300.

"Efficacy of Intravaginal 0.75% Metronidazole Gel for the Treatment of Bacterial Vaginosis", Hillier, Sharon L., Ph.D et al, Obstetrics & Gynecology vol. 81, No. 6 Jun. 1993 (punctum plug 962-967).

Publication, "Low Prevalence of Bacterial Vaginosis-Associated Flora as Detected in Cervical Smears of Moroccan Immigrants, a Population Group Known to Practice Intensive Vaginal Hygiene", Dr. Mathilde E. Boon, Leiden Cytology and Pathology Laboratory, Leiden, The Netherlands, 20 pages.

\* cited by examiner

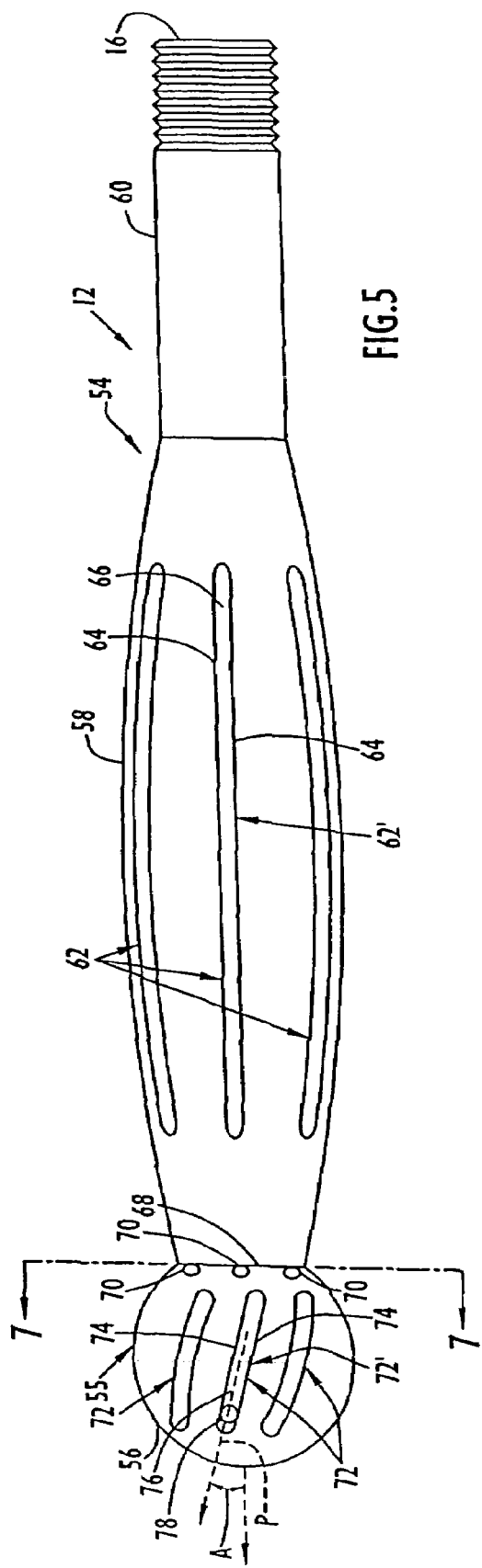
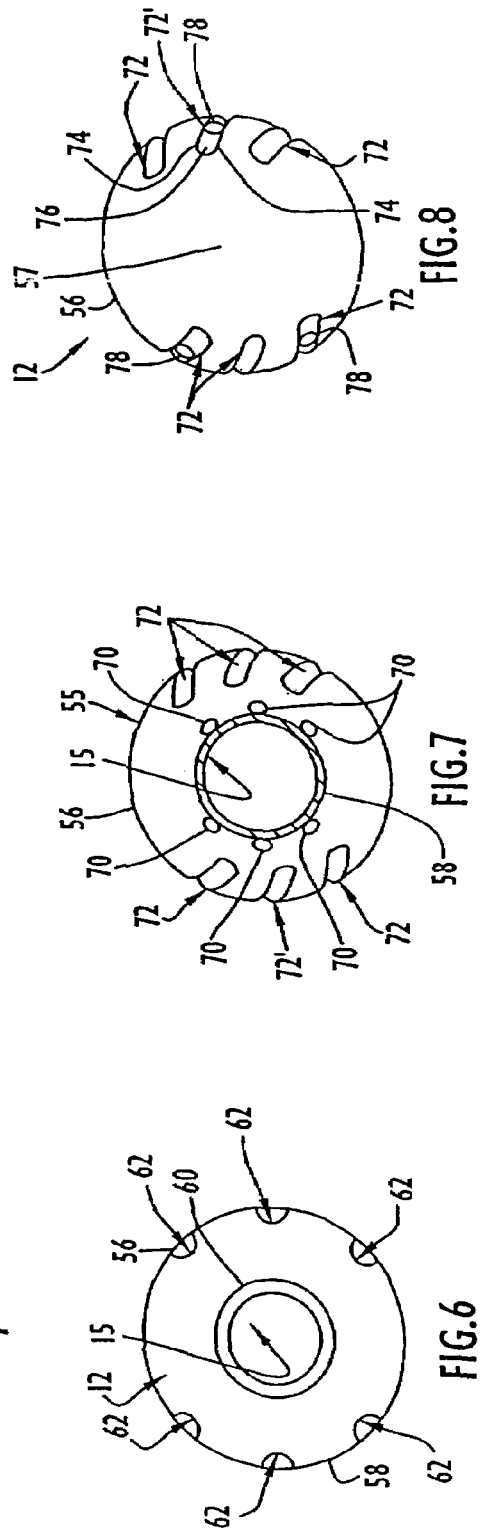

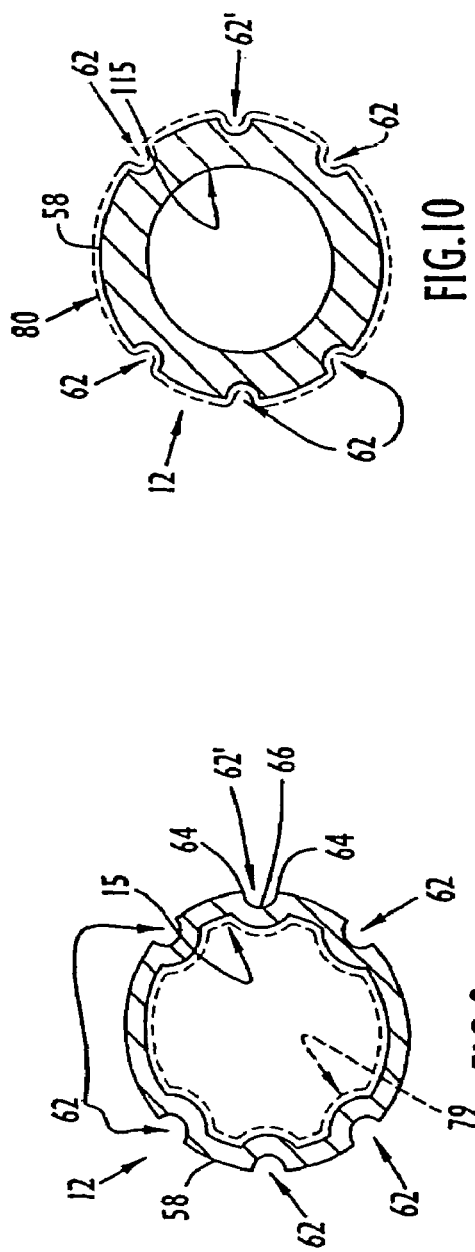
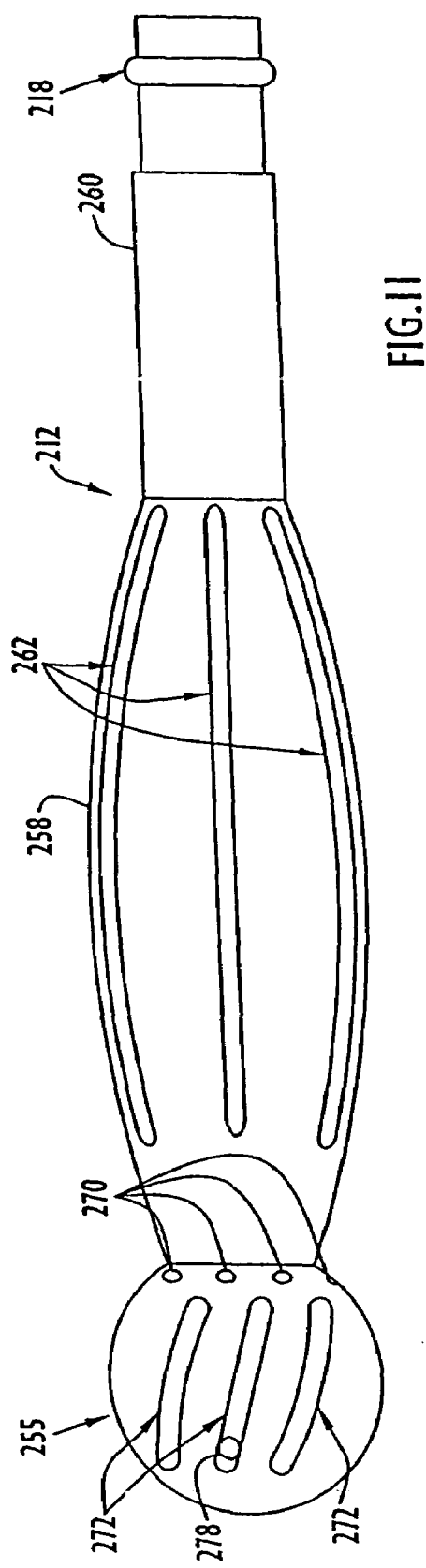

METHODS OF TREATING ABNORMAL BIOLOGICAL CONDITIONS USING METAL OXIDES

CROSS-REFERENCE TO RELATED PATENT APPLICATIONS

This application is a continuation-in-part of prior U.S. patent application Ser. No. 10/371,395 filed Feb. 20, 2003, which is a continuation-in-part of prior U.S. patent application Ser. No. 10/077,256 filed Feb. 20, 2002 and now U.S. Pat. No. 6,589,216. This application claims priority from prior provisional patent application Ser. No. 60/472,167 filed May 21, 2003. The entire disclosures of all of the aforesaid patent applications are incorporated herein by reference.

BACKGROUND OF THE INVENTION

1. Field of the Invention

The present invention relates generally to vaginal douches and, more particularly, to methods of treating abnormal biological conditions arising in and/or affecting the vagina.

2. Brief Discussion of the Related Art

In the area of female personal hygiene and gynecological health, vaginal douches have been proposed for reducing vaginal odors. Conventional vaginal douches typically involve the application of a stream of douching fluid through a vaginal douche applicator and into the vaginal canal of the user. Water alone as a douching fluid is not effective at significantly alleviating vaginal odors when used in conjunction with vaginal douche applicators that do not have a stainless steel external surface. Since it is most typical for vaginal douche applicators to be made of inexpensive disposable materials, such as plastic, conventional vaginal douches usually include various commercial douching agents or substances, such as cleansing and/or disinfecting agents and/or perfumes, to be mixed with water by the user to obtain a douching fluid or supplied to the user as a prepared douching fluid. However, commercial douching agents or substances tend not to be effective in alleviating some vaginal odors or may serve merely to temporarily mask vaginal odors. Even when commercial douching agents or substances are effective in alleviating vaginal odors, the vaginal odors may return shortly after douching.

Another problem associated with many conventional vaginal douches is that the douching agents or substances may cause irritation in some users and/or tend to alter the normal pH (acid/alkaline) or chemical balance of the vaginal canal. When the vaginal canal becomes irritated and/or has its normal pH (acid/alkaline) or chemical balance disturbed or altered, an increased risk is presented for vaginitis, including yeast, bacterial vaginosis and other infections. Vinegar has been proposed as a natural douching agent or substance which, when mixed with water in the proper proportion, presents a douching fluid that closely mimics the normal pH of the vaginal canal. However, douching fluids consisting of vinegar and water tend not to be effective against vaginal odors for any meaningful length of time.

The issue of vaginal odor alleviation is addressed in U.S. Pat. No. 6,290,365 B1 to Abbott et al, the entire disclosure of which is incorporated herein by reference, disclosing the alleviation of vaginal odors by contacting vaginal tissue with a stainless steel surface of a vaginal douche applicator in the presence of water.

A further problem associated with many conventional vaginal douches is that the vaginal douche applicators discharge douching fluid directly at and/or toward the cervix with sufficient force or pressure so that douching fluid may enter the cervical canal. When this occurs, vaginal debris such as bacteria and other harmful or undesirable organisms carried by the douching fluid may pass through the cervix and enter the uterine cavity, potentially causing pelvic inflammatory disease. Where douching fluid is not discharged toward the cervix and the upper portion of the vaginal canal, however, odors will not be eliminated or will quickly return since the cervix as well as the vaginal tissue are responsible for odors. Hence, failure to wash off the cervix and the upper portion, or fornix, of the vaginal canal will yield an incomplete douching. An additional problem of many conventional vaginal douches relates to the inadequacy of the vaginal douche applicators in maintaining an unobstructed gravity flow of douching fluid from the vaginal canal. Since the vaginal canal is normally collapsed or contracted, it has a tendency to clamp down on a vaginal douche applicator inserted therein. Accordingly, douching fluid containing vaginal debris may be prevented from exiting the vaginal canal and may collect and become trapped in the vaginal canal thereby allowing bacteria and other harmful organisms, including those responsible for sexually transmitted diseases, to remain in and move higher in the vaginal canal after douching. During douching, trapped douching fluid may build up in the vaginal canal with a sufficient pressure head that the douching fluid is detrimentally forced into and/or through the cervical canal. Many conventional vaginal douches are also problematic for their failure to limit, regulate or control the flow of douching fluid into the vaginal douche applicators such that the douching fluid is discharged from the applicators at pressures high enough to force the douching fluid into the cervix. Other drawbacks to many conventional vaginal douches are that the vaginal douche applicators are not designed for reuse and are actually unsuitable for reuse due to the difficulties involved in maintaining cleanliness for repeated use.

Normal, balanced vaginal environments are characterized in part by trace numbers of yeast cells, trace numbers of coccoid bacteria called Gardnerella vaginalis and a preponderance of lactobacillus bacteria. Vaginal environments that are disturbed or unbalanced include those having an overgrowth of coccoid bacteria. Coccoid overgrowth is associated with an abnormal biological condition known as bacterial vaginosis, characterized by various symptoms which may be present constantly or may appear intermittently. One out of four women may be infected with bacterial vaginosis, yet 50% of infected women may be asymptomatic. Inflammation associated with bacterial vaginosis may extend to the fallopian tubes and endometrium. Also, the production of amines, such as putrescine and cadaverine, may have a carcinogenic effect, with there being a statistical association between coccoid overabundance and cervicitis and epithelial changes. The effects of bacterial vaginosis are believed to synergize with human immunodeficiency virus (HIV) and human papilloma virus (HPV). In the case of HIV, the presence of bacterial vaginosis may cause increased numbers of virus secreting cells and/or may enhance cell binding by the virus, thereby resulting in an increased risk for HIV transmission. In the case of HPV, the presence of bacterial vaginosis may result in the survival of oncogenic cell mutations related to cervical carcinoma, and research indicates bacterial vaginosis to be a precursor to cervical cancer. Accordingly, the presence of bacterial vaginosis has been linked to increased incidences of cervical cancer and sexually transmitted diseases, and may enable harmful viruses to infect healthy tissue. An excess of yeast cells may lead to problems, one such problem being fungal proliferation or yeast infections characterized by itching, burning and/or abnormal discharge. Unfortunately, health care providers and conventional gynecological tests such as pap smears do not routinely screen for bacterial vaginosis and yeast infections.

A relationship has been established between bacterial vaginosis and recent coitus. Since semen is alkaline, the normal pH of the vaginal canal increases significantly after coitus and changes from mildly acidic to a more alkaline level such that the normal pH (acid/alkaline) of the vaginal environment is unbalanced or disturbed. This higher pH promotes a rapid increase in coccoid production and may result in coccoid overgrowth leading to bacterial vaginosis and its various adverse consequences. Accordingly, postcoital vaginal douching using conventional plastic applicators and commercial douching agents or water to wash away semen and/or coccoid bacteria may have some limited benefit in preventing bacterial vaginosis and/or counteracting already existing bacterial vaginosis but has not been shown to reliably prevent and eliminate bacterial vaginosis. Because of the various problems and limited effectiveness of most conventional vaginal douches, vaginal douching has not been widely adopted and used, particularly in the United States, as a preventative and/or treatment for bacterial vaginosis.

A healthy vagina is moderately acidic, with a normal pH in the range of about 3.5 to 4.5. Where vaginal pH exceeds about 4.5, the vaginal environment may be considered abnormal and is conducive to the development of bacterial vaginosis. On the other hand, a vaginal pH below about 3.5 presents an abnormal environment that is favorable to the development of fungal infections. Normal vaginal flora and pH may be disrupted by many commercial douching agents which tend to kill off beneficial lactobacilli and allow overgrowth of harmful bacteria, by poor hygiene encouraging the overgrowth of harmful bacteria, by increased pH levels resulting from the presence of semen, by wearing tight and/or damp clothing and/or by incorrectly treating a vaginal infection with the wrong medication.

Conventional treatments for bacterial vaginosis include topical and oral antibiotics which possess adverse side effects and promote the development of drug-resistant bacteria. Only about 50% of bacterial vaginosis cases are eliminated in response to conventional treatments and even successfully treated cases tend to recur. It has been shown that about 30% of bacterial vaginosis cases recur after three months and about 80% recur after nine months following conventional antibiotic treatments. Furthermore, conventional antibiotic treatments for bacterial vaginosis may leave patients at increased risk for fungal infections by overcorrecting the vaginal environment. Various over-the-counter anti-fungal products are available to treat fungal infections of the vaginal canal. However, users of conventional anti-fungal products may have their vaginal pH increased too far and may be at increased risk for bacterial infections.

Each type of vaginal infection currently requires its own specific treatment. Unfortunately, the various symptoms of vaginal infection are not recognized by most women, and frequently the infection is not accurately diagnosed by doctors. Too often, healthcare providers and patients incorrectly assume the presence of a yeast infection and seek relief from over-the-counter anti-yeast medication. However, a recent study of 1000 American women who purchased anti-yeast medication showed that only 28% actually had a yeast infection, while the remaining 72% of women had other vaginitis. Using an incorrect medication can often worsen the actual condition. Introducing an anti-yeast medication in the absence of a yeast infection may result in abnormal vaginal flora after only one day. After five days of using the medication, the beneficial lactobacilli may be almost totally eliminated, which makes the underlying bacterial infection even more severe. Diagnosis and treatment of various abnormal biological conditions arising in or affecting the vagina is made more complicated by the fact that the conditions may be asymptomatic.

The treatment of abnormal biological conditions in aqueous environments like the vagina is made more difficult where the organisms responsible for the abnormal conditions are present as biofilm. Biofilm forms when bacteria adhere to a surface in an aqueous environment and begin to excrete a slimy substance that can anchor them to the surface. A biofilm may be formed by a single bacterial species, but more often includes many species of bacteria as well as fungi, algae, protozoa, debris and corrosion products. Once anchored to a surface, biofilm microorganisms may initiate a variety of detrimental reactions. Biofilms are implicated in a significant proportion of human bacterial infections.

Biofilm bacterial behavior is much more complex than planktonic or suspended cell behavior due to colonization of the biofilm organisms. Unlike suspended cells, biofilm organisms live in and populate communities. Recent studies have revealed significant differences in the level of expression of genes involved in nutrient cycling among members of a single species bacterial population exposed to the same apparent conditions. Within these populations, there appears to be a "division of labor" whereby some cells utilize available energy to turn on metabolic pathways that effect partial degradation of dead particulate matter while other cells of the same population utilize the degradation products to produce new cells. A bacterium which attaches to a surface thusly activates a different set of genes which transform it into a significantly different organism than the same bacterium in suspension. Most bacterial on the behavior of suspended cells are less effective on biofilm cells. For example, antibiotic doses which kill suspended cells in humans may need to be increased to prohibitively toxic levels in order to kill biofilm cells, and biofilms have thusly contributed to the problem of drug-resistance. Disinfection rates for biofilm cells are far below the disinfection rates for planktonic cells killed by antimicrobials.

Conventional douching with plastic applicators and commercial douching agents or water may benefit vaginal environments that are already undesirably altered or disturbed, but the benefits derived are very limited and may be outweighed by the many disadvantages of conventional douching. Douching fluids including water, vinegar and/or commercial douching agents used with conventional plastic douche applicators fail to properly normalize and stabilize disturbed vaginal environments and either undercorrect or overcorrect for vaginal disturbances. Conventional douching may temporarily improve one aspect of the vaginal environment while creating imbalances or disturbances in other aspects thereof. The benefits derived from conventional douching are very short-lived, yet conventional douching performed too frequently is potentially harmful in many respects and may actually greatly exacerbate vaginal disturbances. Indeed, the benefits provided by conventional douching generally amount to merely masking the symptoms of vaginal disturbances without a clinically significant correction of the underlying causes of abnormalities.

Accordingly, conventional douching is unsuitable as a treatment and/or preventative for bacterial vaginosis and yeast infections much less other abnormal biological conditions arising in or affecting the vagina.

It is evident from the foregoing that there is a need for more effective treatments for abnormal biological conditions arising in and/or affecting the vagina. There is also a need for a method of treating abnormal biological conditions arising in and/or affecting the vagina wherein the method is capable of treating various different abnormal biological conditions. Another need exists for safe, non-pharmacological treatments for biofilms and other abnormal biological conditions arising in and/or affecting the vagina. A further need exists for methods of treating abnormal biological conditions arising in and/or affecting the vagina where the treatment itself does not contribute to abnormal biological conditions or disturbances.

SUMMARY OF THE INVENTION

The present invention overcomes the disadvantages of prior methods of treating abnormal biological conditions arising in and/or affecting the vagina. The present invention allows simple vaginal douching with water and a vaginal douche applicator having an external surface comprising metal oxide to be used as a primary and/or preventative treatment for many different abnormal biological conditions arising in and/or affecting the vagina. In accordance with the present invention, abnormal biological conditions arising in and/or affecting the vagina may be treated by exposing the vaginal canal to a metal oxide, and the metal oxide may comprise the external surface of stainless steel. The metal oxide may comprise the external surface of a vaginal douche applicator or treatment device through which douching fluid is supplied, and the douching fluid may comprise plain water. Various abnormal biological conditions may be treated pursuant to the present invention including abnormal bacterial conditions, biofilms, pathogenic conditions, neoplastic conditions, fungal conditions, inflammatory conditions, viral conditions, sexually transmitted diseases and disturbed vaginal environments. Treatment according to the present invention may be primary and/or preventative.

Some of the advantages of the present invention are that direct impact of the cervical os with douching fluid is avoided; effective treatment of abnormal vaginal conditions may be achieved using only water as the douching fluid with or without treatment substances or additives, such as pH lowering, pH increasing, antibiotic, antiseptic, probiotic and/or microbicide substances or additives to obtain various additional effects or reactions; treatment substances or additives may be applied to the vaginal canal separately from douching using the vaginal douche applicators or treatment devices to apply the treatment substances or additives; the vaginal douche applicators provide a smearing or spreading effect such that douching fluid and/or treatment substances or additives may be more widely and more uniformly disbursed in the vaginal canal; desquamated cells, debris, bacteria and other harmful or undesirable organisms are flushed out of the vaginal canal; a "leaky" or imperfect seal is maintained between the vaginal douche applicators and the wall of the vaginal canal no matter how tightly the vaginal wall contracts around or clamps down on the vaginal douche applicators; the vaginal douche applicators are innately less expensive since they are reusable; post-coital douching is promoted since the vaginal douche applicators can be used repeatedly on demand; the vaginal douche applicators may be provided with specialized coatings or finishes to obtain various reactions or effects; the same procedure may be used to prevent and/or treat bacterial vaginosis, vaginal yeast infections as well as other abnormal biological conditions arising in and/or affecting the vagina; the problem of treating abnormal vaginal conditions with the wrong treatment is avoided; vaginitis may be treated without the adverse side effects of oral and topical medications; the methods of the present invention are self-limiting, self-regulating or self-stabilizing in that abnormal vaginal environments are not overcorrected or undercorrected; users may safely douche as frequently as desired without any injurious effects; the metal oxide may comprise self-annealing oxide coatings found on the surfaces of metals including metal alloys and stainless steels; the metal oxide may comprise the self-annealing chromium oxide coating found on the surface of stainless steel; vaginal exposure to the metal oxide may be accomplished by contacting vaginal tissue with the metal oxide external surface of a treatment device or applicator; vaginal exposure to the metal oxide may be accomplished by supplying a carrier medium containing particles of the metal oxide to the vagina; and the carrier medium may comprise any suitable biocompatible carrier medium.

The present invention is generally characterized in a method of treating an abnormal biological condition arising in or affecting the vagina comprising the steps of introducing a metal oxide in the vaginal canal and repeating the step of introducing at regular intervals to normalize and/or prevent the abnormal biological condition. The metal oxide may be introduced in the vaginal canal by inserting a treatment device or applicator having an external surface of the metal oxide in the vaginal canal, and water may be supplied to the vaginal canal while the treatment device is disposed therein. The metal oxide may be introduced in the vaginal canal by introducing a carrier medium containing particles of the metal oxide in the vaginal canal. The metal oxide may comprise a self-annealing oxide coating on the external surface of metals including stainless steel and metal alloys. The metal oxide introduced in the vaginal canal causes a natural reaction to occur in the vaginal canal which normalizes abnormal biological conditions and/or maintains the normality of normal biological conditions. The method of treating comprises primary treatment of existing abnormal biological conditions as well as preventative treatment of potential abnormal biological conditions. Abnormal biological conditions treated by the method of treating include fungal, bacterial, biofilm, pathogenic, viral, inflammatory and/or neoplastic conditions. The conditions treated may be symptomatic or asymptomatic. More than one abnormal biological condition may be treated simultaneously. The method of treating may include the step of measuring vaginal pH prior to performing the steps of introducing and repeating. The step of introducing may be repeated at more frequent regular intervals where vaginal pH is above 4.5 or below 3.5 and/or where symptoms of an abnormal biological condition are present. The step of introducing may be repeated at less frequent regular intervals where vaginal pH is in the range of 3.5 to 4.5. In a modified method of treating according to the present invention, the method is performed within eight hours after intercourse. The reaction which occurs in the vaginal canal as a result of the present invention is self-limiting, self-regulating or self-stabilizing in that abnormal biological conditions are normalized without over-correction or under-correction, and normal biological conditions are maintained without creating biological disturbances or abnormalities.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 5 is a side view of a vaginal douche applicator or treatment device of the vaginal douches.

FIG. 6 is a proximal end view of the vaginal douche applicator.

FIG. 7 is a sectional view of the vaginal douche applicator taken along line 7-7 in FIG. 5.

FIG. 8 is a distal end view of the vaginal douche applicator.

FIG. 9 is a cross-sectional view depicting a lumen or passage of the vaginal douche applicator.

FIG. 10 is a cross-sectional view depicting an alternative lumen or passage for the vaginal douche applicator.

FIG. 11 is a side view of an alternative vaginal douche applicator for use in the methods of the present invention.

DESCRIPTION OF THE PREFERRED EMBODIMENTS

Figure 1:
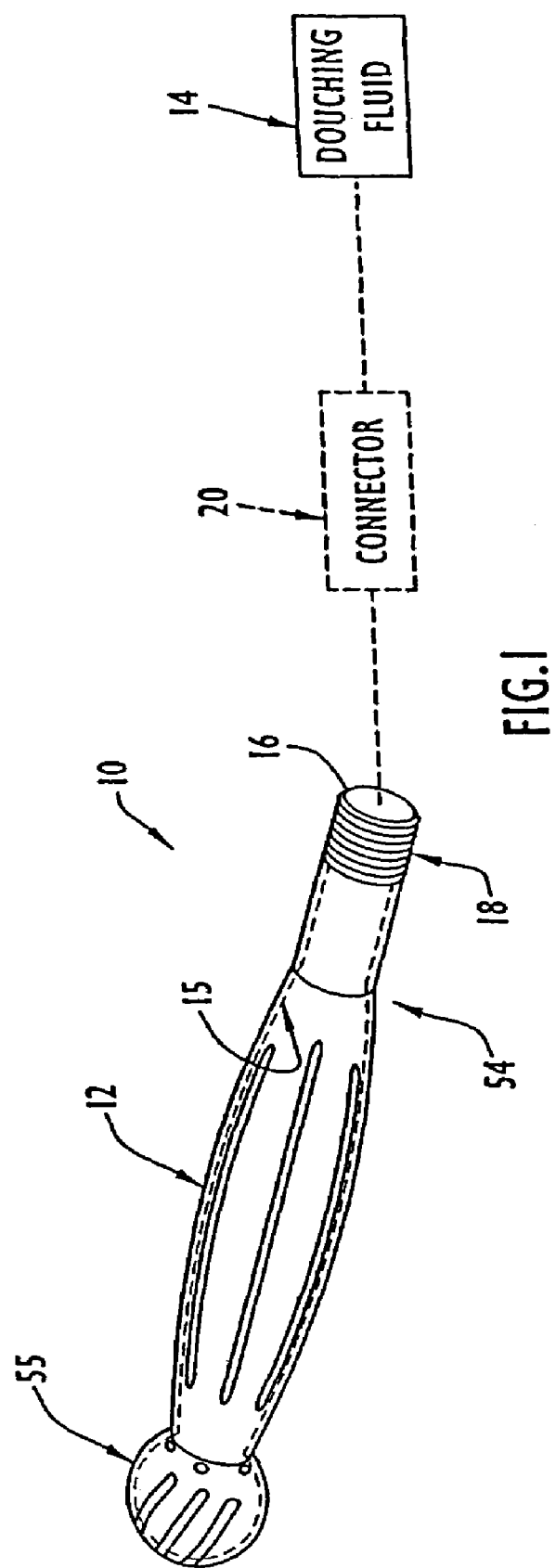
FIG. 1 is an exploded perspective view, partly schematic, of a vaginal douche for use in the methods of the present invention.

A vaginal douche 10 according to the present invention is illustrated in FIG. 1. Vaginal douche 10 comprises a vaginal douche applicator or treatment device 12 and a source or supply 14 of douching fluid coupled with vaginal douche applicator 12. The vaginal douche applicator 12 has a longitudinal passage or lumen 15 therein for being supplied with douching fluid from the source or supply 14. An open proximal end 16 of the vaginal douche applicator 12 provides communication with the passage 15 and may include securing structure 18 to facilitate coupling of the vaginal douche applicator with the source or supply 14. The source or supply 14 may be any suitable source or supply of water, preferably gravity fed from a container, with or without therapeutic additives. A connector 20 may be used to couple the vaginal douche applicator 12 with the source or supply 14, and the design of the connector 20 can vary depending on the source or supply 14. As described further below, the vaginal douche applicator 12 is designed for repeated use.

Figure 2:
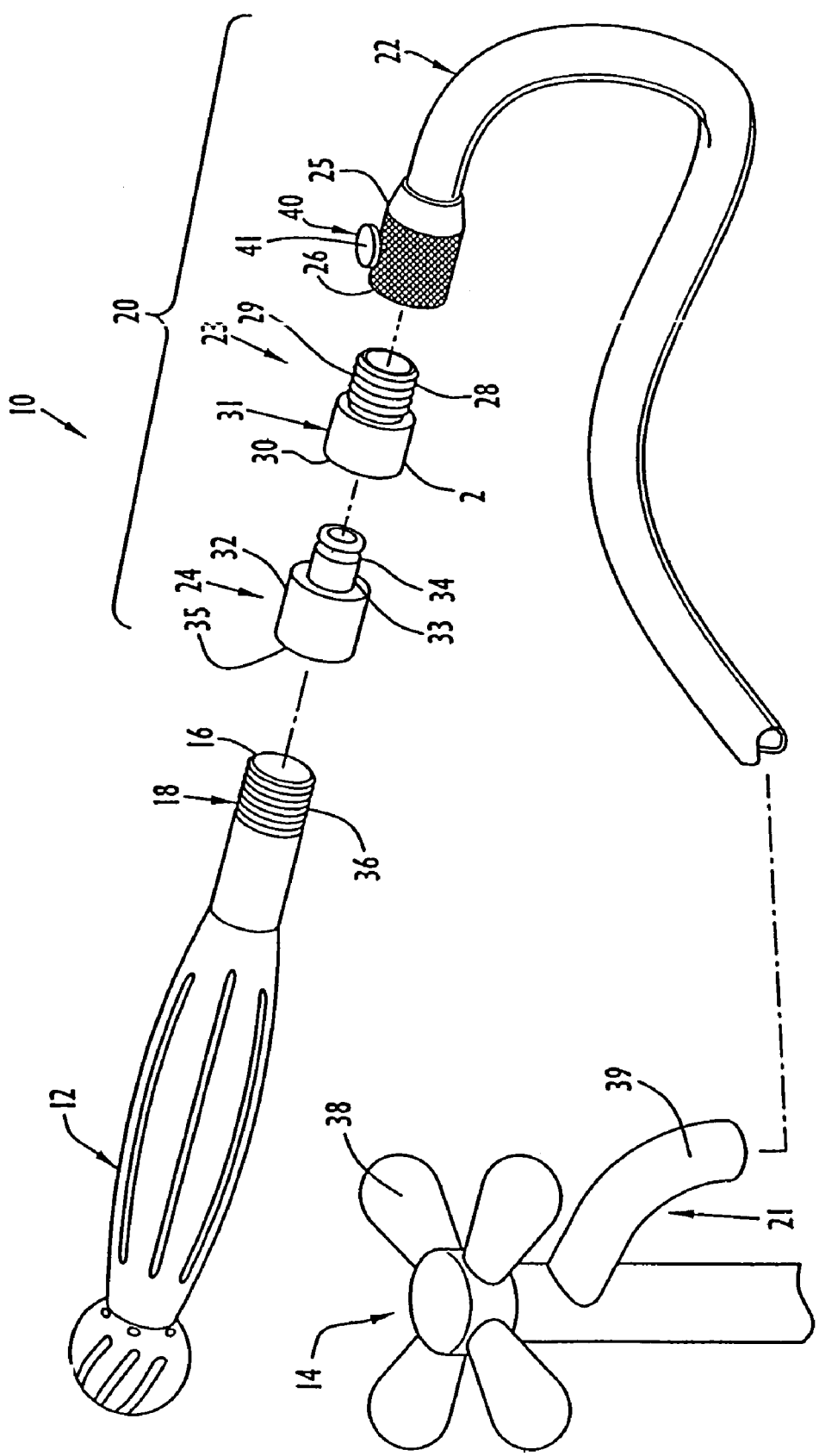
FIG. 2 is an exploded perspective view depicting one version of the vaginal douche.

In one version of vaginal douche 10 illustrated in FIG. 2, connector 20 is designed to couple the vaginal douche applicator 12 with a standard tap or faucet 21 forming the source or supply 14 of douching fluid. The connector 20 is shown exploded in FIG. 2 and comprises a fluid supply conduit 22, a coupling 23 and an adaptor 24. The fluid supply conduit 22 may be designed in many various ways as a hollow conduit, including various tubes and hoses, and is preferably flexible for ease of use. The fluid supply conduit 22 has a proximal end (not shown) releasably connectable with the tap or faucet in a conventional manner and has a distal end carrying a hollow fitting 25. Fitting 25 may have a knurled external surface to facilitate grasping and has an open distal end 26 with an internal thread (not visible in FIG. 2) for releasable threaded connection to coupling 23.

Coupling 23 is hollow and includes a relatively larger diameter cylindrical distal section 27 and a relatively smaller diameter cylindrical proximal section 28 coaxially aligned with distal section 27. Proximal section 28 has an external diameter to fit within the distal end 26 of fitting 25 and has an external thread 29 for releasably, threadedly engaging the internal thread of fitting 25. Distal section 27 includes an open distal end 30 and a longitudinally slidable collar or sleeve 31 biased by an internal spring (not shown) of coupling 23 to be normally disposed in a locking position, shown in FIG. 2, in which one or more detents (not shown), such as balls, within the distal section 27 are held in a radially inward position to protrude into the lumen or interior of the distal section 27. The collar 31 is manually moveable or slidable longitudinally from the locking position to a release position in which the one or more detents are free to move radially outwardly into the wall of distal section 27 so that the one or more detents no longer protrude into the lumen or interior of the distal section 27. When the collar 31 is thereafter released, the collar 31 is automatically returned to the locking position due to the bias of the internal spring, and the one or more detents are also automatically returned to the radially inward position.

The adaptor 24 is hollow and includes a cylindrical distal portion 32 and a cylindrical stem 33 extending proximally from distal portion 32 in coaxial alignment therewith. Stem 33 has an external diameter to fit within the open distal end 30 of coupling 23 and has an external annular or circumferential groove 34. When the collar 31 is in the locking position, protrusion of the one or more detents into the lumen or interior of coupling 23 prevents full insertion of stem 33 into the distal section 27. When the collar 31 is moved to the release position, the stem 33 is able to be fully inserted into the distal section 27 since the one or more detents move radially outwardly and retract into the wall of the distal section 27. Insertion of stem 33 as far as possible into distal section 27 corresponds with alignment of groove 34 with the one or more detents. Accordingly, when the collar 31 thereafter returns to the locking position, the one or more detents are returned to the radially inward position and enter the groove 34. In this manner, the adaptor 24 is releasably connected to the coupling 23 and is releasably locked thereto. The distal portion 32 of adaptor 24 has an open distal end 35 with an internal thread (not visible in FIG. 2), and the lumen or interior of distal portion 32 is of a size to receive the proximal end 16 of vaginal douche applicator 12 in the open distal end 35 of distal portion 32. The securing structure 18 of vaginal douche applicator 12 includes an external thread 36 for releasable threaded engagement with the internal thread of distal portion 32.

The tap or faucet 21 conventionally includes a built-in valve, operable via a knob 38, for controlling fluid flow from a spigot 39. Accordingly, the tap or faucet may be used to selectively control, limit or regulate the force, pressure and/or volume of douching fluid flow supplied to the vaginal douche applicator. However, a more desirable and safer way to control, limit or regulate the force, pressure and/or volume of douching fluid flow from tap or faucet 21 into applicator 12 is a valve or other flow controlling, flow limiting or flow regulating structure provided in or on the applicator and/or the connector. Where a valve is provided in or on the connector shown in FIG. 2, the valve may be provided in or on any of the components of the connector including the fluid supply conduit 22, the coupling 23 and the adaptor 24.

As an example, FIG. 2 illustrates a valve 40 incorporated in the fitting 25 of fluid supply conduit 22. Valve 40 includes an operating member 41 connected to a valve body (not shown) disposed in the lumen or passage of fitting 25. The valve body is spherical and fills the cross-sectional dimension of the lumen or passage of the fitting 25. The valve body has a plurality of intersecting flow passages extending diametrically therethrough, with the flow passages being of different cross-sectional diameters or sizes. The operating member 41 forms an externally located knob or handle that is manually rotatable to correspondingly rotate the valve body about an axis perpendicular to a central longitudinal axis of the fitting 25 to axially align a selected one of the flow passages with the central longitudinal axis of fitting 25. When one of the flow passages is aligned with the central longitudinal axis of the fitting, the remaining flow passage or passages is/are blocked or obstructed by an internal surface of the fitting. The flow passage that is axially aligned with the central longitudinal axis of fitting 25 forms part of and dictates the cross-sectional size of the lumen or passage of fitting 25. In this manner, the operating member 41 is operable to selectively adjust the cross-sectional size of the lumen or passage of fitting 25, thereby controlling, limiting or regulating fluid flow through the fitting 25 into the coupling 23. Visual and/or tactile indicia can be provided at any suitable location or locations to indicate the rotational positions for the operating member 41 corresponding to alignment of the flow passages, respectively, with the central longitudinal axis of fitting 25. Of course, each rotational position for the operating member should correspond to a safe force, pressure and/or volume of douching fluid flow into the vaginal douche applicator to ensure that douching fluid discharged from the vaginal douche applicator is not forced into the cervical canal. The same indicia used to indicate the rotational positions for the operating member, or different visual and/or tactile indicia provided at any suitable location or locations, may be used to provide an indication of the flows, pressures and/or volumes corresponding to the rotational positions, respectively.

The fluid supply conduit 22, the coupling 23 and the adaptor 24 may be the same as or similar to those disclosed in U.S. Pat. No. 6,190,365 B1, to Abbott et al, the entire disclosure of which is incorporated herein by reference. It should be appreciated that the source or supply 14, including a gravity feed container, can be coupled directly to the vaginal douche applicator 12 without a connector as represented in FIG. 1, and that the vaginal douche applicator 12 need not be provided with securing structure 18 or thread 36. The fluid supply conduit 22 can be designed for direct connection to the vaginal douche applicator 12 or to the adaptor 24 and either or both of the adaptor 24 and the coupling 23 can be eliminated. The fluid supply conduit 22 can be of any desired length. In addition, a container containing one or more therapeutic substances or other additives can be coupled between the vaginal douche applicator 12 and the source 14 of douching fluid, as described in the application incorporated herein by reference, for introducing a desired quantity of such one or more additives into the water being used as the douching fluid. The fluid supply conduit 22, the coupling 23, and/or the adapter 24 may be disposable but are preferably reusable for convenience and economy. The fluid supply conduit 22, the coupling 23 and/or the adapter 24 may thusly be made of materials which facilitate cleanliness or sterility.

Figure 3:
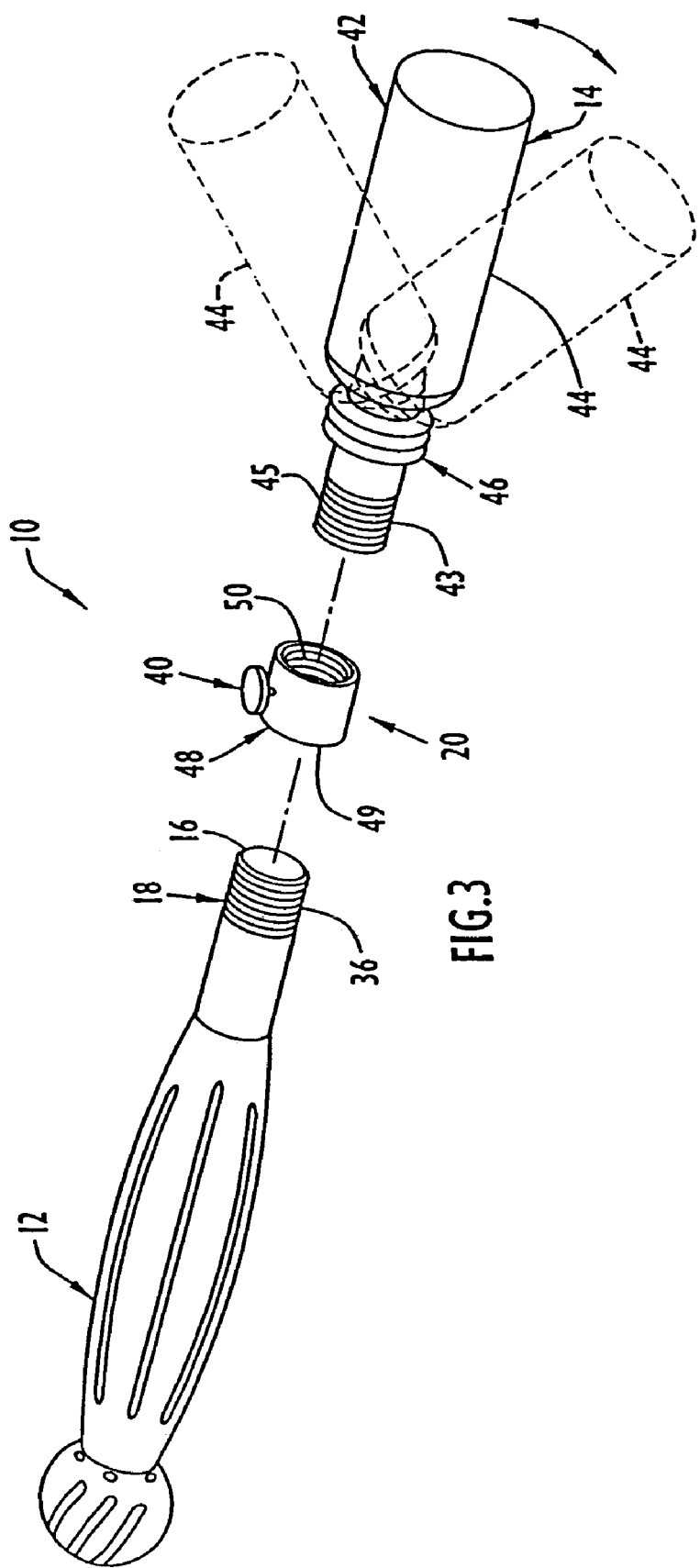
FIG. 3 is an exploded perspective view depicting another version of the vaginal douche.

In another version of vaginal douche 10 illustrated in FIG. 3, the connector 20 is designed to couple the vaginal douche applicator 12 with a container, bottle or bag 42 forming the source or supply 14 of douching fluid. The container 42 contains douching fluid and has a neck 43 extending from a container body 44 to terminate at an open end of container 42. An external thread 45 is disposed on neck 43 adjacent or close to the open end of container 42, and the neck 43 is connected to the container body 44 at a flexible junction 46. Flexible junction 46 allows the container 42 to bend or pivot at junction 46 so that the container body 44 can be selectively angled relative to the vaginal douche applicator 12 for versatility and ease of use. FIG. 3 shows the container 42 in a first position in which the container body 44 is in longitudinal or axial alignment with the neck 43 so that the container body is also in longitudinal or axial alignment with the connector 20 and with the vaginal douche applicator 12. As shown by an arrow in FIG. 3, the container body 44 can be pivoted or rotated about junction 46 to a variety of second positions, two of which are represented in dotted lines, in which the container body is no longer longitudinally or axially aligned with the neck 43 so that the container body is also no longer in longitudinal or axial alignment with the connector 20 and with the vaginal douche applicator 12. As shown by the second positions illustrated in FIG. 3, the container body 44 may be disposed at a desired angle to a central longitudinal axis of the vaginal douche applicator 12. In one of the second positions depicted in FIG. 3, the container body 44 is pivoted upwardly to facilitate establishment of gravity feed of douching fluid from the container 42 into the vaginal douche applicator 12.

The junction 46 is shown as comprising one or more expandable and collapsible pleats formed integrally, unitarily with the container 42, but can be designed in any suitable manner integrally, unitarily with the container or as one or more separate components. Also, the location of junction 46 on the container 42 can be varied. The junction 46 allows the container body 44 to be positioned as needed to facilitate establishment of gravity feed of the douching fluid contained therein into applicator 12. Alternatively or additionally, at least the container body 44 may be flexible to permit the container 42 to be manually squeezed, compressed or collapsed to dispense the douching fluid from the open end thereof. However, a gravity feed is preferred for enhanced safety by better ensuring that the douching fluid is not discharged into the vaginal canal with excessive force or pressure. The container 42 may be reusable but is preferably disposable after use to ensure cleanliness for repeated use by permitting a new container of douching fluid to be coupled with the vaginal douche applicator 12. The container 42 can be coupled directly to the vaginal douche applicator 12, without a connector, as represented by FIG. 1. The container 42 can be designed in many various ways and may have various configurations. In one preferred embodiment, the container is sized to hold thirty two ounces of douching fluid. The container may be designed to be suspended or hung from a hanger or hook, and preferably the container will be mounted or disposed at standing eye level to the user for controlled gravity feed of douching fluid while accounting for users of different heights.

In the vaginal douche 10 of FIG. 3, connector 20 comprises a hollow, cylindrical coupling 48 having an open distal end 49 sized to receive the proximal end 16 of vaginal douche applicator 12. The open distal end 49 has an internal thread (not visible in FIG. 3) for releasable threaded engagement with the external thread 36 of vaginal douche applicator 12. The coupling 48 has an open proximal end sized to receive the open end of container 42, and the open proximal end of coupling 48 has an internal thread 50 for releasable threaded engagement with the external thread 45 of container 42. Coupling 48 includes a valve 40 for selectively controlling the cross-sectional size of the passage or lumen through the coupling 48 in order to selectively control, limit or regulate the force, pressure and/or volume of douching fluid flow from container 42 into the vaginal douche applicator 12. The coupling 48 can be reusable or can be disposable. It is preferred that a reusable coupling be made of a material conducive to cleaning.

Figure 4:
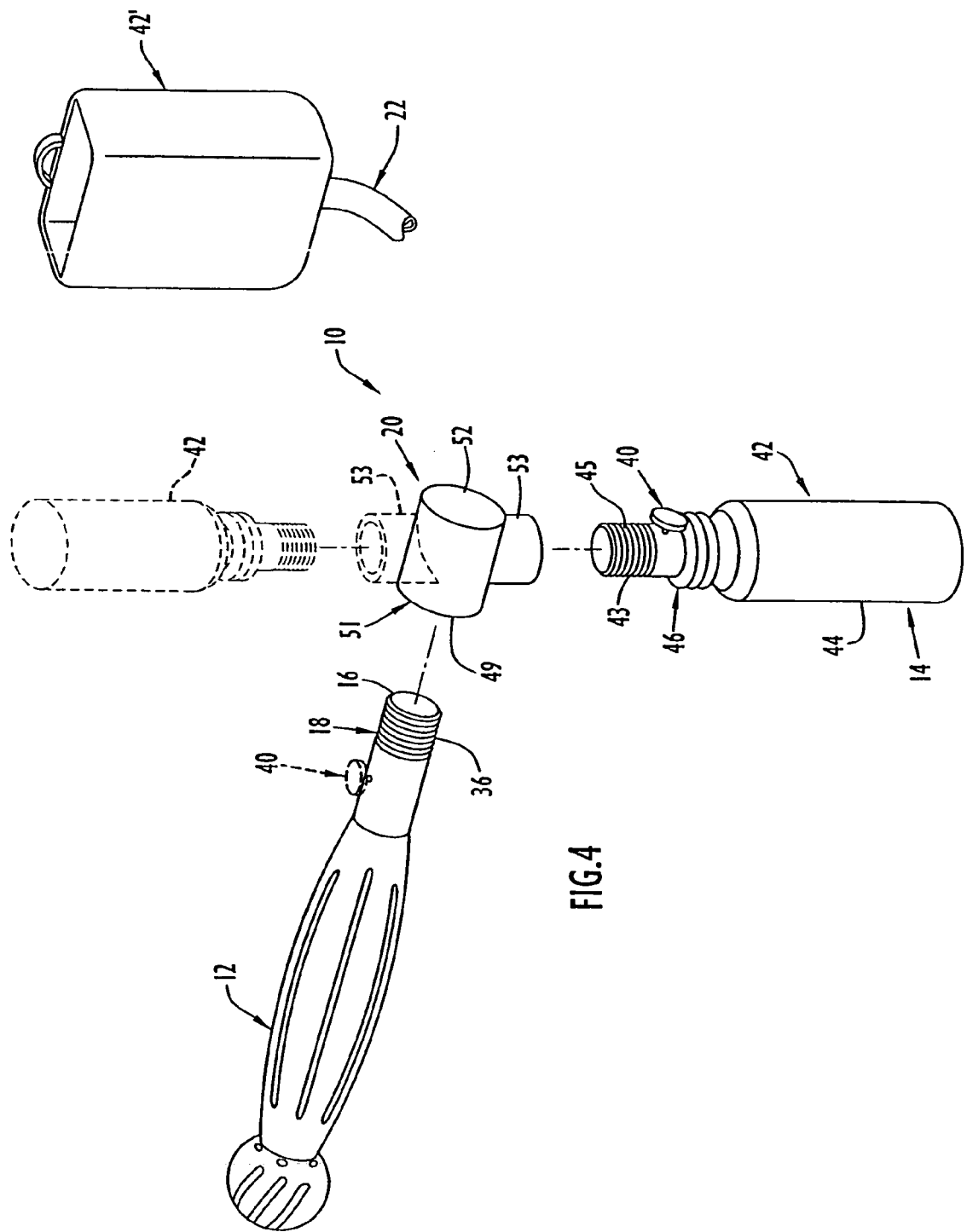
FIG. 4 is an exploded perspective view depicting an additional version of the vaginal douche.

An additional version of vaginal douche 10 is depicted in FIG. 4, in which the connector 20 connects the container 42 to the vaginal douche applicator 12 in a longitudinally offset position. Connector 20 as illustrated in FIG. 4 comprises a hollow coupling 51, which is similar to coupling 48 but has a closed proximal end 52 and a hollow, transverse extension 53. Transverse extension 53 extends perpendicularly from a cylindrical body of coupling 51 and terminates at an open end provided with an internal thread (not visible in FIG. 4). The neck 43 of container 42 fits into the open end of extension 53 with the external thread 45 of container 42 in releasable engagement with the internal thread of extension 53. The cylindrical body of coupling 51 has a central longitudinal axis perpendicular to extension 53, and the interior of the cylindrical body is in communication with the interior of extension 53. The cylindrical body of coupling 51 has an open distal end for releasable threaded engagement with vaginal douche applicator 12 as described for coupling 48. Accordingly, when the container 42 is coupled with the vaginal douche applicator 12 via coupling 51, the container 42 is disposed in a first position perpendicular to the central longitudinal axis of the vaginal douche applicator. However, the angle of the container body 44 with the vaginal douche applicator can be varied by moving the container to a second position in which the container body is pivoted around junction 46. As shown in FIG. 4, the container body 44 may, as an example, be oriented to extend upwardly or downwardly relative to the vaginal douche applicator 12. By orienting the container body 44 to extend upwardly as shown in dotted lines, gravity feed of douching fluid from the container into the vaginal douche applicator can be facilitated. FIG. 4 also illustrates valve 40 provided at neck 43 to control, limit or regulate fluid entering the vaginal douche applicator 12. As shown in dotted lines, valve 40 could be provided at the proximal end of the vaginal douche applicator 12.

FIG. 4 also illustrates a gravity feed container 42' coupled to one end of fluid supply conduit 22, the other end of which is adapted for coupling to the proximal end 16 of vaginal douche applicator 12. The container 42' is preferably sized to hold thirty-two ounces of water and may include an eyelet or other structure by which the container may be suspended or hung at standing eye level to the user. When the vaginal douche applicator 12 is inserted in the vaginal canal of the user when in a standing or seated position, the water from container 42' will be supplied to the vaginal douche applicator 12 and released into the user's vaginal canal by gravity. Gravity feed of water to the vaginal douche applicator is preferred since it ensures that the flow of water released into the vaginal canal is at a safe pressure and eliminates the need for a pressure regulating valve.

As described further below, vaginal douche applicator 12 has an external surface comprising metal oxide. As best illustrated in FIGS. 1 and 5-10, vaginal douche applicator 12 comprises an applicator body 54 having open proximal end 16 and a forward end formed as, joined to or connected with a head or tip 55. Proximal end 16 provides communication with the lumen or passage 15 which extends within applicator body 54 and head 55 as shown in dotted lines in FIG. 1. The passage 15 is supplied with douching fluid from the source or supply 14 with which the proximal end of the vaginal douche applicator is coupled. The passage 15 extends distally from the open proximal end 16 to terminate at an internal distal end surface within head 55. The passage 15 has a central longitudinal axis coaxial with the central longitudinal axis of vaginal douche applicator 12. Head 55 is coaxial with the applicator body 54 and is defined by a wall 56 forming a closed distal end for the vaginal douche applicator, the wall 56 having a substantially spherical external configuration. The center of head 55 is located along the central longitudinal axis of the vaginal douche applicator 12 and is contained in a solid central area 57 of wall 56 shown in FIG. 8.

Applicator body 54 has a tapered distal segment 58 extending proximally from head 55 and a cylindrical proximal segment 60 extending proximally from a rearward end of distal segment 58. The distal segment 58 has a forward end connected to head 55. Distal segment 58 is circular in external cross-sectional configuration, with the external cross-sectional configuration of the distal segment 58 tapering or decreasing toward or in the direction of the forward and rearward ends of the applicator body. In particular, distal segment 58 tapers in external cross-sectional diameter or size forwardly and rearwardly from a maximum external cross-sectional diameter or size at or approximately at the longitudinal center of the distal segment 58 between head 55 and proximal segment 60. The external cross-sectional diameter or size of distal segment 58 tapers relatively gradually closer to the longitudinal center of the distal segment and tapers relatively more steeply closer to the forward and rearward ends of the distal segment. The distal segment 58 thusly has a distal external cross-sectional diameter or size adjacent head 55, i.e. at the forward end of distal segment 58, and has a proximal external cross-sectional diameter or size adjacent proximal segment 60, i.e. at the rearward end of distal segment 58. The distal and proximal external cross-sectional diameters or sizes are smaller than the maximum external cross-sectional diameter or size. The distal external cross-sectional diameter or size may be considered a distal minimum external cross-sectional diameter or size, and the proximal external cross-sectional diameter or size may be considered a proximal minimum external cross-sectional diameter or size. The proximal segment 60 has a circular external cross-sectional configuration corresponding to the proximal minimum external cross-sectional diameter or size of distal segment 58. The proximal segment 60 terminates proximally at an opening into proximal end 16, and the external cross-sectional configuration and size of the proximal segment is uniform or constant between distal segment 58 and the opening.

A plurality of external body channels 62 are disposed along the external surface of the distal segment 58. Each body channel 62 is formed by a longitudinally extending groove or flute which follows the external contour of the distal segment 58 and extends in the same direction as the central longitudinal axis of the vaginal douche applicator. Each body channel 62 has a width between a pair of opposing, longitudinally extending side edges 64 and has a curved or radiused bottom surface 66 with a radius of curvature from a point external of the vaginal douche applicator 12 as shown in FIGS. 5 and 9 for body channel 62'. The width and/or depth of each body channel 62 preferably tapers at forward and rearward ends of the body channel such that the forward and rearward ends of the body channels merge or blend into the external surface of the distal segment 58. Each body channel 62 has a length between its forward and rearward ends, with each body channel extending longitudinally or lengthwise along a substantial portion of the length of distal segment 58. The forward ends of body channels 62 are spaced rearwardly from head 55. The rearward ends of body channels 62 may be spaced forwardly from proximal segment 60 as shown for vaginal douche applicator 12 or may extend to the proximal segment as described below for the vaginal douche applicator 212. Each body channel 62 is bisected longitudinally by a radial plane, i.e., a plane radial to the central longitudinal axis of vaginal douche applicator 12, and has a central longitudinal axis disposed in the radial plane. The vaginal douche applicator 12 includes six like channels 62 arranged around the central longitudinal axis of vaginal douche applicator 12. The body channels 62 could be equally spaced or irregularly spaced about the central longitudinal axis of the vaginal douche applicator. In the illustrated embodiment, the body channels 62 are irregularly spaced and are arranged in two groups disposed on opposite sides of the applicator body with each group having three body channels, i.e. a central body channel disposed between two side body channels. Each group of body channels has its side channels spaced a first circumferential distance from its central channel. The side channels of one group are spaced from corresponding side channels of the other group by a second circumferential distance which is greater than the first circumferential distance.

Head 55 is substantially spherical in external configuration with a rearward end 68 joined to the forward end of distal segment 58. The head 55 has an external maximum diametric dimension perpendicular to the central longitudinal axis of vaginal douche applicator 12 that is the same as or substantially the same as the maximum external cross-sectional diameter or size of distal segment 58. A plurality of discharge or outlet holes or passages 70 are formed in wall 56 at the rearward end of head 55 and may thusly be considered rearward or proximal discharge or outlet holes or passages, the rearward discharge holes 70 being disposed close to or adjacent the forward end of distal segment 58. The holes 70, which communicate with the passage 15, are shown as being disposed at, in contact with or in abutment with the forward end of distal segment 58 and are thusly disposed at, in contact with or in abutment with the minimum distal external cross-sectional diameter of distal segment 58. However, the holes 70 can be disposed close to but spaced slightly forwardly from the forward end of distal segment 58. Each hole 70 is shown as having a circular cross-sectional configuration; however, the holes 70 can have a non-circular cross-sectional configuration. Particularly where the holes 70 are at, in contact with or in abutment with the forward end of distal segment 58, the holes 70 may have circular or non-circular cross-sectional configurations including partial and semi-circular cross-sectional configurations. Preferably, six holes 70 are provided in head 55 at equally spaced or irregularly spaced radial locations around the distal segment 58 as best shown in FIG. 7, which is representative of irregularly spaced rearward discharge holes. Accordingly, the center of each hole 70 is disposed in a radial plane, i.e., a plane radial to the central longitudinal axis of vaginal douche applicator 12. The holes 70 face proximally and outwardly toward the applicator body 54 and are arranged on head 55 with each hole 70 preferably aligned or substantially aligned in the longitudinal direction with a respective body channel 62 as shown for applicator 12. It should be appreciated, however, that the holes 70 can be offset from the body channels 62 in the longitudinal direction such that each hole may be disposed between a respective pair of adjacent body channels. It should also be appreciated that the number of holes 70 can vary in that more than six holes or less than six holes can be provided in head 55. Depending on the number of holes 70, a hole 70 can be aligned in the longitudinal direction with each body channel 62 as well as there being a hole 70 between each pair of adjacent body channels 62 as described below for vaginal douche applicator 212.

A plurality of external head channels 72 are disposed along the external surface of wall 56. As shown in FIG. 8, the head channels 72 have forward ends disposed around the solid central area 57 of wall 56 which forms the closed distal end of the vaginal douche applicator. Each head channel 72 extends proximally from its forward end to a rearward end, with each head channel 72 extending along a substantial portion of the length of head 55 as measured from the distal end of vaginal douche applicator 12 to the forward end of distal segment 58. The rearward end of each head channel 72 may be aligned or substantially aligned in the longitudinal direction with a forward end of a corresponding body channel 62. Each head channel 72 has a width between opposing side edges 74 and has a curved or radiused bottom surface 76 with a radius of curvature from a point external to the vaginal douche applicator 12 as shown in FIGS. 5 and 8 for head channel 72'. The forward ends and the rearward ends of head channels 72 preferably blend into or merge with the external surface of head 55 as described above for body channels 62. Each head channel 72 is angled from distal to proximal in the same direction such that the head channels 72 have a helical arrangement on head 55. The head channels may be equally spaced or irregularly spaced from one another about the central longitudinal axis of the vaginal douche applicator, with central longitudinal axes of the head channels 72 contained in planes P, respectively, disposed at a helix angle A to the plane containing the central longitudinal axis of the vaginal douche applicator 12 as shown in FIG. 5 for head channel 72'. Accordingly, the head channels 72 extend in a direction transverse to the central longitudinal axis of the vaginal douche applicator so that the head channels 72 are transverse to the body channels 62. Also, the planes P are non-radial to the central longitudinal axis of the vaginal douche applicator. When the vaginal douche applicator 12 is viewed from the side with the distal end thereof on the left as shown in FIG. 5, the head channels 72 are angled downwardly from distal to proximal. Six head channels 72 are provided in head 55 with the head channels arranged in two groups of three head channels each on opposite sides of head 55 as described above for body channels 62. Each group of head channels 72 is disposed on a side of head 55 corresponding to a side of applicator body 54 on which a group of body channels 62 is disposed.

Every other or alternate head channel 72 has a forward outlet or discharge hole or passage 78 therein spaced proximally from the solid central area 57 of wall 56 and from the forward ends of the head channels and spaced distally from the rearward discharge holes 70. Forward discharge holes 78 open along the bottom surfaces 76 of the corresponding head channels 72 and communicate with the lumen or passage 15 of vaginal douche applicator 12. The forward discharge holes 78 may be equally spaced or irregularly spaced from one another in a radial or rotational direction, the forward discharge holes 78 being representative of irregularly spaced forward discharge holes. One group of head channels 72 has a forward discharge hole located in its central head channel while the other group of head channels 72 has a forward discharge hole in each of its side head channels as best depicted in FIG. 8. The forward discharge holes face distally and face outwardly from head 55 at angle A, which may be considered a helix angle or transverse angle, to the central longitudinal axis of the vaginal douche applicator. The diameter or cross-sectional size of forward discharge holes 78 is sufficiently large to ensure a relatively low pressure flow of douching fluid therefrom as explained further below. The forward discharge holes 78 may have circular or non-circular cross-sections.

FIGS. 1 and 9 illustrate passage 15 as being of non-uniform or variable cross-sectional configuration and size along the entire length thereof. It should be appreciated, however, that the cross-sectional configuration and size of passage 15 can be uniform or constant between proximal end 16 and the internal distal end surface. In the case of non-uniform passage 15, the lumen or passage 15 has a cross-sectional configuration corresponding to the external cross-sectional configuration of the applicator body 54 in that the wall of the vaginal douche applicator 12 is of uniform thickness throughout. The vaginal douche applicator 12 may have an internal coating or finish 79 along the internal wall or surface that defines passage 15 as represented by dotted lines in FIG. 9. Internal coating or finish may be a germ-resistant coating or finish or any other coating or finish that facilitates cleanliness and hygiene, preferably preserving cleanliness of the vaginal douche applicator interior between uses. A particularly preferred internal coating is an antimicrobial internal coating. An internal coating may comprise an impregnation or dispersal of one or more selected substances or elements in the material used to form the internal surface or wall or may comprise a discrete surface coating of one or more selected substances or elements over or upon the internal surface or wall. An internal finish may comprise one or more characteristics obtained from various finishing processes including mechanical, chemical, electrical and thermal finishing processes. Representative antimicrobial substances which may be used as an internal coating include AGION silver ion complex and copper alloy. A representative internal finish is electro polishing which, where the internal surface is stainless steel, further enhances the smooth and slippery characteristics of the stainless steel internal surface so that bacteria slide off and cannot take hold to colonize.

FIG. 10 illustrates the vaginal douche applicator 12 with an alternative lumen or passage 115 of uniform or constant cross-sectional configuration and size. In the case of passage 115, the wall forming the vaginal douche applicator 12 is of non-uniform cross-sectional thickness as depicted in FIG. 10. FIG. 10 also illustrates the vaginal douche applicator 12 with an optional external coating or finish 80, shown in dotted lines, which may be the same as the internal coating or finish described above. The external finish should be a steel passivazation first followed by electro polishing or hand polishing.

In a preferred embodiment of vaginal douche applicator 12, the vaginal douche applicator is about 6.0 inches long from its distal end to its proximal end 16, with the proximal segment 60 being about 0.50 inch in length, the distal segment 58 being about 4.63 inches in length, and the head 55 being about 0.87 inch in length. The maximum external cross-sectional diameter of distal segment 58 and the external diametric dimension of head 55 is about 0.93 inch, with the maximum external cross-sectional diameter of distal segment 58 being located about 2.01 inches proximally from head 55. The distal minimum external cross-sectional diameter is about 0.50 inch, and the proximal minimum cross-sectional diameter is about 0.31 inch. Body channels 62 have a length of about 2.35 inches, with the length of body channels 62 being centered or substantially centered within the length of the distal segment 58. Body channels 62 and head channels 72 have a maximum width of about 0.12 inch and a depth of about 0.06 inch. The radius of curvature for the bottom surfaces 66 and 76 is about 0.06 inch. The helix angle A is 30°. The rearward discharge holes 70 have a diameter of about 0.06 inch, and the forward discharge holes 78 have a diameter of about 0.09 inch. The forward discharge holes 78 are located about 0.23 inch proximally of the distal end of the vaginal douche applicator. The first circumferential distance is about 0.48 inch and the second circumferential distance is about 0.53 inch. The vaginal douche applicator has a uniform wall thickness in the range of about 0.001 to 0.01 inch.

An alternative vaginal douche applicator or treatment device according to the present invention is illustrated in FIG. 11 at 212. Vaginal douche applicator 212 is similar to vaginal douche applicator 12 with the exception that the maximum cross-sectional diameter of distal segment 258 and the external maximum diametric dimension of head 255 are larger than that for vaginal douche applicator 12. Also, head 255 and proximal segment 260 for vaginal douche applicator 212 are greater in length than head 55 and proximal segment 60. The body channels 262 for vaginal douche applicator 212 are different from body channels 62 in that the rearward ends of channels 262 extend to the proximal segment 260. In addition, head 255 has a greater number of rearward discharge holes 270. The securing structure 218 for vaginal douche applicator 212 is different than securing structure 18 and comprises an annular boss. In a preferred embodiment for vaginal douche applicator 212, the vaginal douche applicator 212 is about 6.0 inches long. The maximum external cross-sectional diameter for distal segment 258 and the maximum external diametric dimension for head 255 are about 1.2 inches. Head 255 is about 1.0 inch long, and distal segment 258 is about 3.375 inches long. Preferably, eight rearward discharge holes 270 are provided in vaginal douche applicator 212, with the rearward end of each head channel 272 disposed between a pair of adjacent rearward discharge holes 270.

The external surface of the vaginal douche applicators 12, 212 comprises metal oxide. At least the portion of the external surface of the applicators 12, 212 that is disposed in the vaginal canal comprises metal oxide, and preferably the entire external surface of the vaginal douche applicators comprises metal oxide. The metal oxide external surface may be formed by a self-annealing coating of metal oxide on the external surface of metals and metal alloys, including stainless steel. The metal oxide coating may comprises a chromium rich oxide passivation coating resulting from selective diffusion of chromium to the external surface of stainless steel during the formation process. The metal oxide may comprise chromium oxide, i.e. a ceramic, but may comprise other self-annealing oxide coatings on the external surface of metals and metal alloys. The body of the vaginal douche applicators 12, 212 may thusly be made in its entirety of stainless steel or another suitable metal or metal alloy having an external surface of metal oxide. Alternatively, the body of the vaginal douche applicators 12, 212 may have an outer layer of stainless steel or other suitable metal or metal alloy having an external surface of metal oxide along the external surface of the vaginal douche applicators.

The vaginal douches and vaginal douche applicators are used for vaginal douching. As described by way of example for vaginal douche 10, the vaginal douche applicator 12 is coupled with the source or supply 14 of douching fluid (not shown in FIG. 12), which will typically be only plain water for routine use. The use of plain water alone as the douching fluid ensures minimal alteration of normal vaginal pH while washing out some bacteria and sperm. However, the douching fluid may include additives, such as pH lowering substances, to inhibit growth of non-acid loving bacteria. A culture of lactobacilli could be added to the douching fluid to assist lactobacilli proliferation and offset the washout of beneficial bacteria. Other additives which may be added to the douching fluid include pH altering substances, antiseptic substances, antimicrobial substances, antibiotics, probiotics and/or microbicides. Any of the foregoing additives or substances could be applied to the vaginal canal subsequent to douching using the vaginal douche applicator to apply the additives or substances as explained further below.

Figure 12:
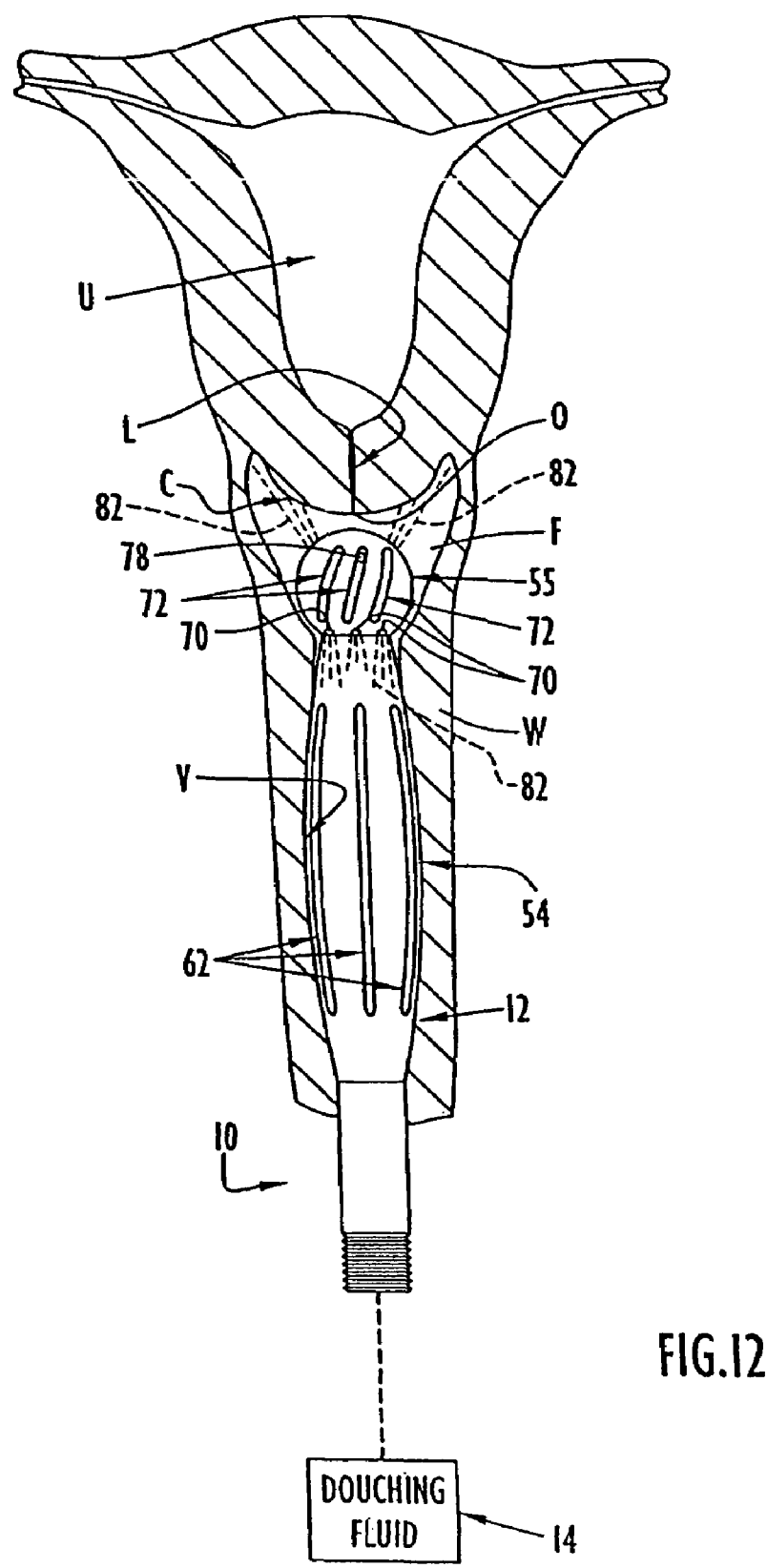
FIG. 12 is a broken view, partly in section, illustrating use of the vaginal douche in the methods according to the present invention.

Once the vaginal douche applicator 12 is coupled with the source or supply 14 of douching fluid, the distal end of the vaginal douche applicator 12 is inserted through the vaginal opening into the vaginal canal V. The vaginal douche applicator 12 is advanced into the vaginal canal to a comfortable, safe insertion distance in which the head 55 is disposed within or adjacent the upper portion or fornix F of the vaginal canal V as shown in FIG. 12. In this position, the solid central area 57 of head 55 is aligned or substantially aligned with the cervical os O leading into the cervical canal L. The vaginal wall W produces a "squeegee" effect around the head 55 during insertion of the vaginal douche applicator 12 in the vaginal canal V, thusly providing a self-cleaning effect which deters the transfer of harmful or undesirable organisms from the lower portion to the upper portion of the vaginal canal. The configuration and contour of the applicator body 54 expands the vaginal canal V and maximizes the surface area of vaginal tissue and mucosa in contact with the external surface of the applicator along an interface between the vaginal wall W and the vaginal douche applicator 12. Accordingly, the reaction of the vaginal environment with the metal oxide external surface of the applicator will also be maximized. Although contact between the vaginal douche applicator 12 and the vaginal wall W is maximized, the vaginal douche applicator 12 maintains a "leaky" or non-fluid tight seal or fit with the vaginal wall. In particular, the body channels 62 prevent a successful or complete seal of vaginal wall W around the external surface of the vaginal douche applicator 12, no matter how tightly the vaginal wall clamps down on the vaginal douche applicator.

Douching fluid from the source or supply 14 is supplied to the lumen or passage 15 through the open proximal end 16 of the vaginal douche applicator 12, and the douching fluid exits or is discharged from the vaginal douche applicator into the vaginal canal V through the rearward and forward discharge holes 70 and 78. As discussed above, flow of douching fluid into the vaginal douche applicator 12 can be controlled, regulated or limited via valves or other flow regulating structure and/or gravity feed containers, thereby preventing discharge of douching fluid from the applicator at pressures high enough to force the douching fluid into the cervical canal L of cervix C.

As shown in FIG. 12, douching fluid 82 is discharged from rearward discharge holes 70 and forward discharge holes 78 as drizzle rivulets effecting a drizzle flow effect from head 55 at a low rate and pressure. The douching fluid 82 discharged from the rearward discharge holes 70 into the vaginal canal V creates a sheeting effect over the external surface of the vaginal douche applicator, as facilitated by the tapered external contour of applicator body 54. The sheeting effect that is created from the rearward discharge holes 70 floods the external surface of the applicator body 54 with optimally directed, low pressure douching fluid flow along the interface between the vaginal wall W and the applicator body 54. Consequently, the external surface of the applicator body 54 is maximally surface flooded with a thin film of douching fluid, and the tissue/external surface interface is maximally flooded to enhance reaction of the metal oxide with the vaginal tissue. The vaginal douche applicator 12 also achieves very low pressure washing of the fornix F and the cervix C. The angle of forward discharge holes 78 from the central longitudinal axis of the vaginal douche applicator 12 prevents douching fluid 82 discharged from the forward discharge holes 78 from directly impacting the cervical os O. Also, the solid central area 57 of head 55 acts as a barrier to isolate the cervical os O so that douching fluid does not directly impact the cervical os and enter the cervical canal L. The douching fluid 82 discharged from forward discharge holes 78 is discharged at an angle to the cervical os O and is directed toward and streams off of the sides of the cervix C into and along the vaginal wall forming fornix F, thereby washing the upper portion of the vaginal canal V. Since the cervix C and fornix F are gently washed, cervical and vaginal secretions are diluted and/or flushed from the vaginal canal V.

Discharged douching fluid 82 streams back to head 55 and is directed along head channels 72 to the body channels 62. Discharged douching fluid 82 is directed along the body channels 62 toward the vaginal opening for exit from the vaginal canal V. The body channels 62 and head channels 72 thusly maintain a gravitational rinsing or cleansing flow of douching fluid 82 out of the vaginal canal V. The gravitational flow should be established by the user's body position; for example, the douching method should be preformed while standing or sitting upright so that the user's torso is upright or erect. The flow of douching fluid 82 out of the vaginal canal V flushes or rinses desquamated cells, debris, sperm, bacteria and other undesirable organisms from the vaginal canal. Since a retrograde or gravitational flow of douching fluid from the vaginal canal V is maintained, flow of douching fluid 82 toward the cervix C, particularly the cervical canal L, is minimized so that douching fluid and organisms carried thereby are prevented from being driven upwardly from the lower portion of vaginal canal V to the cervix C. In addition, the channels 62 and 72 prevent douching fluid from becoming trapped and accumulating or building up in the vaginal canal V.

In a representative method, approximately thirty-two ounces of douching fluid is discharged into the vaginal canal during douching and, upon completion of douching, the vaginal douche applicator 12 is withdrawn from the vaginal canal V. The vaginal douche applicator is cleaned on the inside and on the outside, and soap and water can be used for cleaning. The vaginal douche applicator 12 may then be stored for future or repeated use on demand. The vaginal douche applicator 212 is used in essentially the same manner as that described for applicator 12.

Vaginal odors are neutralized due to contact of the metal oxide external surface of the vaginal douche applicators with vaginal tissue in the presence of water. In particular, contact of the metal oxide external surface of the vaginal douche applicators 12, 212 with the vaginal tissue in the presence of water causes natural, ionization or chemical reactions with odor linked chemical bonds that results in breakage of the odor linked chemical bonds and neutralization of their odor carrying capabilities. Since it is desirable to preserve the lactobacilli, additives can be used during or subsequent to douching to encourage the growth of lactobacilli as discussed above. However, this is not necessary since normal vaginal pH may be achieved and maintained due to the presence of the metal oxide in the vaginal canal. In addition to neutralizing vaginal odors, the vaginal douches, the vaginal douche applicators and the methods of vaginal douching and deodorization can be used as a primary or preventative treatment for bacterial vaginosis, particularly when douching is performed post-coital, as described further below. Post-coital douching in accordance with the present invention not only washes sperm from the vaginal canal V, thereby lowering pH and inhibiting coccoid production, but causes a natural reaction which increases the production of lactobacilli over coccoid bacteria and normalizes vaginal flora and pH, while also providing an anti-pathogenic effect. Vaginal douching according to the present invention in the presence of bacterial vaginosis not only flushes coccoid bacteria and lactobacillus bacteria from the vaginal canal V, thusly lowering the coccoid population to more normal levels and allowing the lactobacilli population to proliferate until a balance is achieved, but actually eliminates bacterial vaginosis due to the natural reaction that occurs in the vaginal canal.

Subsequent to or apart from douching, the vaginal douche applicators can be used as applicators to introduce or apply one or more therapeutic substances in the vaginal canal V. Representative therapeutic substances include lactobacilli, pH lowering, pH increasing, antiseptic, antibiotic, probiotic and/or microbicide substances. The therapeutic substances may be provided as a treatment fluid of various viscosities including gels. A preselected quantity or dose of treatment fluid may be provided in a container, such as container 42, capable of being coupled with the vaginal douche applicator 12, 212. The treatment fluid is supplied to the lumen or passage of vaginal douche applicator 12, 212 introduced in the vaginal canal V. As described above for douching fluid 82, the treatment fluid is discharged into the vaginal canal V, and the vaginal douche applicator 12, 212 provides a smearing or spreading effect such that the treatment fluid is widely and uniformly dispersed in the vaginal canal. After the treatment fluid has been dispersed in the vaginal canal V, the vaginal douche applicator 12, 212 is withdrawn from the vaginal canal and cleaned for future use.

In a method according to the present invention of treating abnormal biological conditions arising in or affecting the vagina, water is introduced into the vaginal canal while a treatment device having an external surface of metal oxide is disposed in the vaginal canal. The metal oxide external surface used in the method of treating is as described above for the vaginal douche applicators 12,212. The vaginal douche applicators 12, 212 or any other vaginal douche applicator having an external surface of metal oxide can be used as the treatment device, with water being supplied to the vaginal canal via the treatment device. However, it should be appreciated that the treatment device does not have to be a vaginal douche applicator and that water can be supplied to the vaginal canal independent and separate from the treatment device. As used herein, "abnormal biological conditions" is intended to comprise symptomatic and asymptomatic abnormal fungal, bacterial, biofilm, viral, inflammatory and neoplastic conditions arising in and/or affecting the vagina. Representative but not limiting fungal conditions comprise yeast and *candida albicans*; representative but not limiting bacterial conditions comprise *Gardnerella vaginalis,* bacterial vaginosis, *Listeria monocytogenes,* Mycoplasma, Ureaplasma, beta-hemolytic *Streptococcus, Staphylococcus aureus, Treponema pallidum, Haemophilus ducreyi* and any non-lactobacilli bacterial pathogen including bacterial sexually transmitted diseases such as gonorrhea (*Neisseria gonorrhoeae*), syphilis, *Chlamydia* and *Trichomonas vaginalis*; representative but not limiting viral conditions include DNA and RNA viruses, cytomegalovirus and viral sexually transmitted diseases including HIV, HPV, herpes simplex type 1 and type 2; representative but not limiting inflammatory conditions comprise vaginitis, vaginismus, pelvic inflammatory disease (PID), atrophic vaginosis, vulvovaginitis, vulvadynia (VVD) and vulvavestibulitis; representative but not limiting neoplastic conditions include vulvar, vaginal and cervical dysplasias including abnormal squamous cells of undetermined significance (ASCUS). The term "biofilm" is intended to encompass biofilms including biofilms having any of the aforementioned organisms. The term "treating" and its derivatives is intended to comprise primary treatment of existing abnormal biological conditions as well as preventative treatment against potential abnormal biological conditions arising in and/or affecting the vagina.

In a method of treating abnormal biological conditions according to the present invention, the treatment device having an external surface of metal oxide is introduced into the vaginal canal through the vaginal opening. FIG. 12 illustrates the treatment device comprising vaginal douche applicator 12 inserted through the vaginal opening into the vaginal canal V in the manner previously described above, with the vaginal wall W contacting the metal oxide external surface of the vaginal douche applicator. With the treatment device properly inserted in the vaginal canal, a flow of water is supplied to the vaginal canal causing a natural reaction to occur therein, which normalizes abnormal biological conditions and maintains the normality of normal biological conditions in the vagina. The reaction that occurs has various beneficial effects including increasing the production of lactobacilli, normalizing or maintaining the normality of vaginal flora and pH, eliminating or decreasing the presence of pathogens, eliminating or decreasing the organisms responsible for the abnormal biological conditions, preventing, eliminating or reducing biofilms and/or strengthening the body's natural defenses against abnormal biological conditions arising in or affecting the vagina. The water may be supplied through the treatment device as described above and as shown in FIG. 12 for vaginal douche applicator 12 and may comprise plain tap water without any additives. Preferably, the treatment device is allowed to remain in the vaginal canal for the length of time required to release about thirty-two ounces of water into the vaginal canal by gravity feed.

It is also preferred that the treatment device be manipulated or moved within the vaginal canal as the water is supplied thereto, and most preferably the treatment device is moved longitudinally, rotationally and laterally within the vaginal canal. Longitudinal movement is accomplished by moving the treatment device distally and proximally along its longitudinal axis in a reciprocating motion. Rotational movement is accomplished by rotating the treatment device about its longitudinal axis. Lateral movement is accomplished by moving the treatment device latitudinally or side to side. Rotational movement may comprise rotation in one direction or oscillatory rotation in opposite directions.

The treatment device is withdrawn from the vaginal canal upon termination of the flow of water to the vaginal canal. Where symptoms of vaginitis, such as bacterial vaginosis and yeast infections, are present in the user prior to the method of treating being performed, the procedure is preferably repeated at least every two days and more preferably every day for 7 to 21 days until symptoms disappear. Where no symptoms are present in the user, the procedure may be repeated less frequently but should still be repeated at regular intervals as a preventative to abnormal biological conditions including fungal, bacterial, viral, inflammatory and neoplastic conditions.

As seen from the above, abnormal biological conditions arising in or affecting the vagina are treated according to the present invention by introducing a metal oxide in the vaginal canal and repeating the step of introducing at regular intervals. In the method described above, the step of introducing is accomplished by introducing a treatment device having a metal oxide external surface in the vaginal canal, supplying water to the vaginal canal while the treatment device remains disposed therein and thereafter withdrawing the treatment device from the vaginal canal. It should be appreciated, however, that the metal oxide can be introduced in the vaginal canal in other ways. For example, in another method of treating according to the present invention, particles of the metal oxide, independent of the stainless steel or other metal base, may be mixed with a carrier medium which is introduced in the vaginal canal. The oxide particles may be mixed in solution or suspension, for example, and the carrier medium may be any appropriate pharmaceutical or biocompatible medium.

The treatment device or applicator can be fabricated as a carrier or substrate having the metal oxide carried thereon as an external surface, layer or coating, and the substrate may be made of plastic to reduce cost. FIG. 11 illustrates by way of example the treatment device 212 fabricated as a hollow plastic substrate 290 carrying an outer layer or coating 292 having an external surface of metal oxide such as chromium oxide. The outer layer or coating 292 can be the metal oxide in its entirety, or the outer layer or coating may comprise an inner layer of the base metal and an external surface layer of the metal oxide, such as chromium oxide. Accordingly, the applicators of the present invention can be fabricated as plastic substrates coated in stainless steel.

The methods of treating according to the present invention are self-regulating, self-controlling or self-stabilizing in that abnormal biological conditions are normalized without over-correction or the creation of other abnormalities or disturbances. The reaction that occurs due to the present invention achieves and maintains normal ranges for the biological conditions without causing the biological conditions to shift outside of the normal ranges for extended periods of time. Accordingly, the reaction provided by the present invention does not cause abnormalities to occur in normal biological conditions. When the methods of the present invention are used as a preventative where no abnormalities are present, the normal biological conditions are thusly maintained without adverse consequences.

The methods of treating may include testing for vaginal pH each time the methods are performed. Vaginal pH testing may be accomplished using conventional pH test strips having a color indicator which may be compared to a color differentiated pH chart or scale. Accordingly, prior to introducing the metal oxide in the vaginal canal, the method of treating may include the steps of inserting a test strip in the vaginal canal, contacting the vaginal wall with a color indicator of the test strip for approximately five seconds to moisten the color indicator, withdrawing the test strip from the vaginal canal, and comparing the color of the color indicator to the colors on the pH chart to obtain a value for the vaginal pH. The value for the user's vaginal pH will be the value indicated on the pH chart for the color that matches or most closely matches the color of the color indicator. A vaginal pH of about 3.5 to 4.5 in a user without symptoms is generally indicative of a normal vaginal environment, and performing the methods of treating at less frequent regular intervals for prevention or maintenance is all that should be needed to maintain vaginal health. Obvious symptoms and/or a vaginal pH greater than 4.5 or lower than 3.5 will typically indicate the presence of bacterial vaginosis or yeast infections, and preferably the methods of treating should be performed at more frequent regular intervals until the measured vaginal pH falls within the normal range. For sexually active women, it is recommended that the methods of treating be performed within 8 hours after each intercourse.

The vaginal douche applicators of the present invention can be made in their entireties of any suitable medically safe metal or can be provided with outer layers of any suitable medically safe metal forming a self-annealing external surface of metal oxide. The metal may comprise stainless steel and various metals and metal alloys. Although it is desirable for the vaginal douche applicators to have metal oxide external surfaces in order to treat abnormal biological conditions by exposure of the vaginal tissue to the metal oxide, it should be appreciated that the external surfaces of the vaginal douche applicators do not have to have a metal oxide coating where only the benefits of applicator configuration are sought. The applicator bodies can be formed integrally, unitarily with the heads, or the applicator bodies and heads can be formed as separate components. The vaginal douche applicators are constructed without any sharp edges or corners to avoid injury or trauma to anatomical tissue. Various seals can be used in any of the components of the vaginal douches to prevent or deter leakage. The vaginal douche applicators can be coupled to the fluid supply conduits in any suitable manner, and the applicators can have any suitable proximal end configuration for being coupled to the conduits. Many various types of valves and/or other flow regulating structures can be used in any of the components of the vaginal douches to control fluid flow including ball cock valves and flapper valves. The valves can be pre-set to obtain a preselected flow rate or can be adjustable by the user to obtain variable flow rates. The vaginal douche applicators are reusable and are, therefore, inherently less expensive than disposable vaginal douche applicators. Reusability of the vaginal douche applicators promotes more frequent douching, particularly post-coital douching, since the applicators remain available for use on demand and eliminate the need for advanced planning and purchases. The external surfaces of the applicators, particularly where passivized, electro polished and/or hand polished, are preferably non-porous, smooth and slippery such that maintaining cleanliness of the vaginal douche applicators between uses is facilitated.

In as much as the present invention is subject to various modifications, additions or changes in detail, the preferred embodiments described herein should be considered illustrative only and should not be taken in a limiting sense since various modifications can be made thereto without departing from the scope of the invention as defined by the appended claims.

What is claimed is:

1. A method of treating an abnormal biological condition arising in or affecting the vagina, comprising the steps of
   introducing into the vaginal canal a treatment device having an external surface of metal oxide formed as a coating on stainless steel;

supplying water to the vaginal canal;

contacting vaginal tissue with the metal oxide external surface as the water is supplied to the vaginal canal with the purpose of causing a natural reaction in the vaginal canal resulting from the combined presence of metal oxide and water in the vaginal canal;

causing the natural reaction to occur in the vaginal canal resulting from the combined presence of the metal oxide and water;

withdrawing the treatment device from the vaginal canal after the water has been supplied thereto;

repeating said steps of introducing, supplying, contacting, causing and withdrawing at regular intervals; and normalizing the abnormal biological condition in response to the natural reaction.

2. The method recited in claim 1 wherein said step of supplying includes supplying the water through the treatment device and discharging the water from the treatment device into the vaginal canal.

3. The method recited in claim 2 wherein said step of supplying includes supplying about thirty-two ounces of water by gravity feed.

4. The method recited in claim 1 wherein said step of contacting includes moving the treatment device within the vaginal canal.

5. The method recited in claim 4 wherein said step of moving includes moving the treatment device longitudinally, latitudinally and rotationally.

6. The method recited in claim 1 wherein said step of normalizing includes reducing the presence of at least one of an abnormal fungal, bacterial, biofilm, viral, inflammatory or neoplastic biological condition.

7. A method of treating an abnormal biological condition arising in or affecting the vagina, comprising the steps of introducing into the vaginal canal a treatment device having an external surface containing metal oxide and having stainless steel beneath said external surface;

supplying water to the vaginal canal;

contacting vaginal tissue with the metal oxide external surface as the water is supplied to the vaginal canal with the purpose of causing a natural therapeutic reaction in the vaginal canal resulting from the combined presence of metal oxide and water in the vaginal canal;

causing the natural reaction to occur in the vaginal canal in response to the combined presence of the metal oxide and water;

withdrawing the treatment device from the vaginal canal after the water has been supplied thereto;

repeating said steps of introducing, supplying, contacting, causing and withdrawing at regular intervals; and treating an asymptomatic abnormal biological condition in response to the natural reaction.

8. The method recited in claim 7 wherein said step of treating includes treating at least one of an asymptomatic fungal, bacterial, biofilm, viral, inflammatory or neoplastic biological condition.

9. The method recited in claim 8 wherein said step of introducing includes introducing a treatment device including a vaginal douche applicator and said step of supplying includes supplying the water through the vaginal douche applicator.

10. The method recited in claim 9 wherein said step of introducing includes introducing a vaginal douche applicator having said external surface formed as a coating on stainless steel.

11. The method recited in claim 8 wherein said step of treating includes reducing the presence of the organisms responsible for the asymptomatic abnormal biological condition.

12. The method recited in claim 8 wherein said step of treating includes preventing the asymptomatic abnormal biological condition.

* * * * *